United States Patent
Wong et al.

(10) Patent No.: US 6,740,527 B1
(45) Date of Patent: *May 25, 2004

(54) METHODS AND REAGENTS FOR CYANIDE-FREE DETERMINATION OF HEMOGLOBIN AND LEUKOCYTES IN WHOLE BLOOD

(75) Inventors: Show-Chu Wong, Sunnyvale, CA (US); Sylvia Khoo, Newark, CA (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1198 days.

(21) Appl. No.: 08/863,121

(22) Filed: May 27, 1997

Related U.S. Application Data (63) Continuation of application No. 08/533,579, filed on Sep. 25, 1995, now abandoned, which is a continuation of application No. 08/275,466, filed on Jul. 14, 1994, now abandoned.

(51) Int. Cl.[7] .......................... G01N 33/48; G01N 33/72
(52) U.S. Cl. ........................... 436/17; 435/2; 435/7.24; 435/7.25; 435/962; 435/967; 436/8; 436/10; 436/18; 436/50; 436/63; 436/66; 436/74; 436/176; 436/826
(58) Field of Search ..................... 435/2, 7.24, 7.25, 435/962, 967, 975; 436/8, 10, 17, 18, 19, 50, 63, 66, 74, 176, 826; 424/93.71, 93.73

(56) References Cited

U.S. PATENT DOCUMENTS

| | | | |
|---|---|---|---|
| 3,652,222 A | * 3/1972 | Denney et al. | ................ 436/97 |
| 3,874,852 A | 4/1975 | Hamill | |
| 4,102,810 A | * 7/1978 | Armstrong | |
| 4,185,964 A | 1/1980 | Lancaster | ..................... 436/17 |
| 4,200,435 A | 4/1980 | Stroupe et al. | ................ 436/67 |
| 4,255,385 A | 3/1981 | Stroupe et al. | ................ 422/61 |
| 4,286,963 A | 9/1981 | Ledis et al. | ..................... 436/63 |
| 4,485,175 A | 11/1984 | Ledis et al. | ..................... 436/63 |
| 4,521,518 A | 6/1985 | Carter et al. | ..................... 436/10 |
| 4,853,338 A | 8/1989 | Benezra et al. | ................ 436/16 |
| 4,962,038 A | 10/1990 | Carter et al. | ................... 436/10 |
| 5,227,304 A | * 7/1993 | Wong | .......................... 436/17 |
| 5,242,832 A | 9/1993 | Sakata | .......................... 436/17 |
| 5,250,437 A | 10/1993 | Toda et al. | .................... 436/10 |
| 5,336,518 A | * 8/1994 | Narayanan et al. | ............ 623/1 |

FOREIGN PATENT DOCUMENTS

| | | |
|---|---|---|
| EP | 0184787 A | 6/1986 |
| EP | 0424871 A | 5/1991 |
| EP | 0444241 A | 9/1991 |

OTHER PUBLICATIONS

Database WPI, Week 9318, Derwent Publication Ltd., London, GB; AN 93–149936 & SU,A,1 707 544 (Onocology Res. Inst.) Jan. 23, 1992.
Patent Abstracts of Japan, vol. 11, No. 107 (P–563), Apr. 4, 1987, JP61254862, Nov. 12, 1986.
Oshiro, et al."New Method for Hemoglobin Determination by Using Sodium Laury Sulfate (SLS)"; Clin. Biochem. 15 (1); 83–88; 1982.
Oshiro, et al. "Sodium Lauryl Sulfate–Hemoglobin"; Sysmex Journal; vol. 13, No. 2; 220–227; 1990.
Bunn & Forget; "Hemoglobin: Molecular, Genetic and Clinical Aspects"; W. B. Saunders Co.; 638–644; 1986.
Merck Index; 10th Edition; 703, 1100.
Aldrich Catalog; 1992–1993 Edition; 701.

* cited by examiner

Primary Examiner—Christopher L. Chin
Assistant Examiner—James L. Grun
(74) Attorney, Agent, or Firm—David L. Weinstein; Michael J. Ward (57) ABSTRACT

Cyanide-free reagents for the determination of hemoglobin and leukocytes present in a blood sample comprise an aqueous solutions of at least one quaternary ammonium salt, preferably selected from the group of alkyltrimethylammonium salts, alkyldimethylbenzylammonium salts or alkylpyridium salts consisting of tetradecyltrimethyl ammonium bromide (TTAB), dodecyltrimethyl ammonium chloride, cetyltrimethyl ammonium bromide, hexadecyltrimethyl ammonium bromide and benzalkonium chlorides, and hydroxylamine salts, especially hydrochloride, sulfate and phosphates and other acid salts. The method involves mixing the reagent with a diluent-diluted blood sample, presenting it to an absorbance spectrophotometer and measuring the resulting optical density as an indicator of hemoglobin concentration. This cyanide-free reagent could be used solely for hemoglobin determinations, or, it can also be used in leukocyte counting and sizing using hematology instrumentation.

5 Claims, 3 Drawing Sheets

METHODS AND REAGENTS FOR CYANIDE-FREE DETERMINATION OF HEMOGLOBIN AND LEUKOCYTES IN WHOLE BLOOD

This application is a continuation of application Ser. No. 08/533,579, filed Sep. 25, 1995, now abandoned which is a continuation of application Ser. No. 08/275,466, filed Jul. 14, 1994, now abandoned.

TECHNICAL FIELD

The present invention is directed to methods and reagents which are useful in the determination of hemoglobin and leukocytes in whole blood samples. More particularly, the present invention relates to cyanide-free reagents for use in the rapid formation of a stable and detectable chromogen which is indicative of the amount of hemoglobin present in a whole blood sample by conventional methodology. In addition, the present invention is suitable for leukocyte determinations as well as for hemoglobin measurements. The reagents and methods are particularly suited to application to automated hematology instruments, especially instruments which utilize the same aliquot of whole blood sample with a lyse reagent adapted for both hemoglobin and leukocyte determinations.

BACKGROUND OF THE INVENTION

The reference or standard methods for determining white blood cell (WBC) counts and hemoglobin (Hb) determinations traditionally utilize reagents containing potassium cyanide (KCN) or other cyanide containing compounds. These cyanide compounds can be hazardous to use because they can produce toxic hydrogen cyanide (HCN). These compounds can also be difficult to dispose of due to the environmentally toxic cyanide content.

Therefore, investigators have been working to develop alternative reagents, which do not contain cyanide. These efforts, however, have certain limitations for application in high-throughput automated instruments which process large numbers of samples, or in a slower methods performed manually or by semi-automated instruments. The chromogen compounds produced by some of these reagents may be formed too slowly in the absence of cyanide or the chromogen produced may be unstable or inconsistent during the period of testing. Additionally, these alternative reagents may not be capable of performing Hb and WBC determinations with the same whole blood sample without making modifications to the instrument hardware or software.

There is, therefore, a great need for a method and reagent system which is free of cyanide and yet reliable for the in vitro analysis of blood utilized by currently available hematology instruments.

The throughput of current automated hematology instruments requires the use of methods and reagents exhibiting rapid reactions rates. For example, the hemoglobin sample turnover rate of an Abbott Laboratories Cell-Dyn® 3000 instrument is approximately twelve (12) seconds. Abbott Laboratories Cell-Dyn® 1600 and 3500 instrument systems take approximately twenty-four (24) seconds for hemoglobin determinations. In addition, most of these instruments call for the same blood sample aliquot and reagent systems to be used for both the white blood cell size and population determinations, as well as the concentration of hemoglobin in the erythrocytes. Current hematology analyzers often utilize the same dilution and reaction mixtures of whole blood and reagent for both hemoglobin determination and white blood cell counting and sizing.

The "standard" lysing/hemoglobin reagent typically contains ingredients to properly lyse the erythrocytes to permit accurate leukocyte counting, and a cyanide containing compound for the formation of a stable chromogen (cyanmethemoglobin) to enable precise colorometric analysis of the hemoglobin content in the erythrocytes. Therefore, in order for a new lysing reagent to be practical, it must be easily adopted for use in existing automated and semi-automated hematology instruments without alteration of either the instrumentation or the performed methodologies. Consequently, there are many significant requirements which must be met by a cyanide-free lysing reagent. Some of these are:

1. The chromogen produced should have maximum absorbance between 530 nm and 550 nm, which is the optimal absorbance range for cyanmethemoglobin of the majority of current, automated methodologies.
2. The chromogen produced should not only be quick to form, but also be fairly stable for a period of at least five minutes to provide good, reproducible results in automated or semi-automatic methods of hemoglobin and leukocyte determinations.
3. The lysing reagent should not interfere with the formation of the hemoglobin chromogen and cannot adversely affect the leukocytes' stability during leukocyte sizing and counting procedures.

SUMMARY OF THE INVENTION

Methods are provided for making Hb and WBC determinations and compositions comprising diluting a whole blood sample with a diluent and mixing the whole blood sample/diluent with an aqueous lyse reagent comprising from about 0.1 to about 20% by weight of at least one quarternary ammonium salt selected from the group consisting of: tetradecyltrimethyl ammonium bromide (TTAB), dodecyltrimethyl ammonium chloride, cetyltrimethyl ammonium bromide, hexadecyltrimethyl ammonium bromide, benzalkonium chloride, cetylpyridium chloride and from about 0.1 to about 15% weight of hydroxylamine salts selected from the group consisting of: hydrochloride, sulfate, phosphate and other acid salts. A chromogen is formed, detected and measured thereby indicating Hb concentration in the whole blood sample as well as WBC population and subpopulation determinations. In addition, compositions are provided of multipurpose cyanide-free lyse reagents which can be utilized in various instrumentations.

DETAILED DESCRIPTION OF THE INVENTION

The present invention makes an ideal multipurpose lysing reagent for use in hemoglobin and leukocyte determinations on various instruments utilizing differing timing and reaction protocols. The performance of this method is comparable to current methods utilized by Cell-Dyn® and Coulter Electronics instruments and commercially available lytic agents. The multipurpose lysing reagent of the present invention has shown excellent stability against freezing and heating, and storage up to 15 months at 60° C. It also exhibits rapid reaction times (5–6 seconds to stabilize) and produces a chromogen absorbing at about 545 nm. The only necessary permutation is the optimization of the concentrations of reagents for particular instruments.

The present invention entails a solvent and at least one diluent and a lyse reagent. The diluent is used to dilute a whole blood sample prior to hemoglobin and leukocyte determination. The solvent is used to make the lyse reagent an aqueous solution before the lyse reagent contacts red blood cells in the diluted whole blood test sample. Typically, the diluent is an inorganic or organic salt solution. The solvent is typically deionized water. For purposes of clarity, the term diluent used hereinafter refers to a salt solution unless otherwise noted.

The lysing reagent of the present invention is comprised of an aqueous solution of one or more quaternary ammonium salts and hydroxylamine salts. The lysing reagent is typically used in combination with a diluent. This combination of lysing reagent and diluent has been shown to be important for the reagent system to meet its specific requirement of hemoglobin and leukocyte determinations. A selective buffer, and other ingredients, may be desirably added to the diluent to be used in combination with the lysing reagent in order to maintain the optimum overall solution pH and osmolality of the reagent system: For instance, in order to obtain a very stable chromogen reaction time to meet an important requirement for manual or a semi-automated method of hemoglobin determination, the combination of tetradecyltrimethyl ammonium bromide (TTAB) lysing reagent and a phosphate isotonic diluent can be used.

The quaternary ammonium salts useful in the present invention are selected from the group of alkyl triethylammonium salts, alkyldimethylbenzylammonium salts and alkylpyridium salts consisting of: tetradecyltrimethyl ammonium bromide (TTAB), dodecyltrimethyl ammonium chloride, cetyltrimethyl ammonium bromide, hexadecyltrimethyl ammonium bromide, benzalkonium chloride, cetylpyridium chloride and other quaternary ammonium salts.

The quaternary ammonium salt, or salts, should be present in the lysing reagent at a total concentration range preferably between 0.1 and 20% weight (wt.). The specific concentration depends on the characteristics of the particular hematology system and on the operational procedure in which the reagent system is employed. The hydroxylamine salt should be added to the lysing reagent to maintain a concentration preferably between 0.1 and 15% (wt.). The hydroxylamine salt is added to speed up the stabilization of the chromogen that is formed upon erythrolysis. Once again, the specific concentration will be determined by the hematology system in which the lysing reagent is to be employed.

Buffers may also be used in the diluents. The specifically preferred buffer depends on the particular hematology system in which the diluent is employed and the performance requirement of that instrument. Generally, the buffer will have a pKa between 6.2 and 8.0, a concentration between 5 and 25 millimolar (mM), pH of 6.5 to 7.5 and the buffer diluent has an osmolality between 250 and 350 milliosmoles/kilogram (mOsM/kg). Some biological buffers employed in the present reagent system include N-[2-Acetamido]-2-iminodiacetic acid (ADA), 3-[N-Morpholino]propanesulfonic acid (MOPS), N,N-bis[2-Hydroxyethyl]-2-aminoethanesulfonic acid (BES), N-[2-Hydroxyethyl]piperazine-N'-[2-ethanesulfonic acid] (HEPES), Piperazine-N,N'-bis[2-ethanesulfonic acid (PIPES), bis[2-Hydroxyethyl]imino-tris[[hydroxymethyl]-methane (Bis-Tris), triethanolamine, imidazole, borate and phosphate. The most preferred buffers are ADA and imidazole.

The method of the present invention is straightforward. A whole blood sample is treated with a diluent. A lysing reagent is prepared by dissolving a specific quantity of quarternary ammonium salts and hydroxylamine salts in a solvent. The lysing reagent is mixed with the diluted whole blood sample, and then the mixed sample is presented to a hemoglobin flow cell (absorbance spectrophotometer) for the measurement of optical density between 540 and 550 nanometers (nm). The optical density measurements are then correlated to hemoglobin concentrations. The result is reported as a measured weight per volume of whole blood. The lysing reagent is prepared by dissolving a specific quantity of quaternary ammonium salts and hydroxylamine salts in a solvent. Generally, the solvent used to dissolve the salts is deionized water.

One of the characteristics enabling the substitution of the cyanide-free reagent of the present invention for the cyanide-containing reagents of the prior art is the absorbance of the chromogen produced by the cyanide-free reagent. Absorbance curves for various reagents are presented in FIG. 1. Curve 1 corresponds to the cyanide-containing reference reagent (Cell-Dyn® Rapid Lyse, Abbott Laboratories, Abbott Park, Ill. 60064). Curve 2 corresponds to the lysing reagent of the present invention. Curve 3 represents data for the sodium dodecyl sulfate lyse of Oshiro et al. Curve 4 was generated with data for the polycarboxylic acid with quaternary ammonium salt lysing reagent described in U.S. Pat. No. 4,185,964. Curve 5 represents data from TTAB, a quaternary ammonium bromide alone in the reagent. Curve 6 was generated with the reagent described in U.S. Pat. No. 5,250,437, with 0.5% sodium nitrite.

Figure 1:
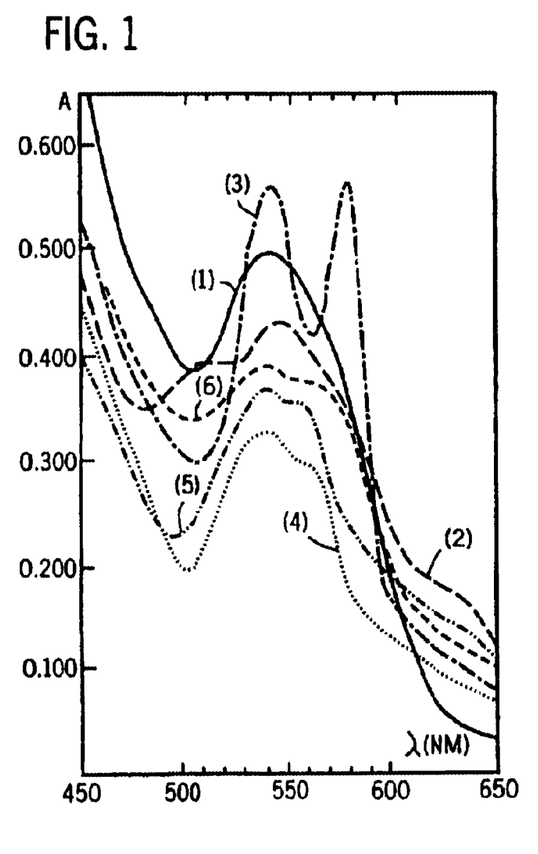
FIG. 1 is a spectrum showing absorbance curves for normal whole blood samples treated with various chromogen-forming reagents, including the reagent of the present invention, which demonstrates that the lysing reagent of the present invention has an absorbance range in the same range as exhibited by presently available lysing agents (at 530–550 nm.)

FIG. 1 illustrates that the lysing reagent of the present invention produces the desired absorbance characteristics between 530 and 550 nm.

Figure 2:
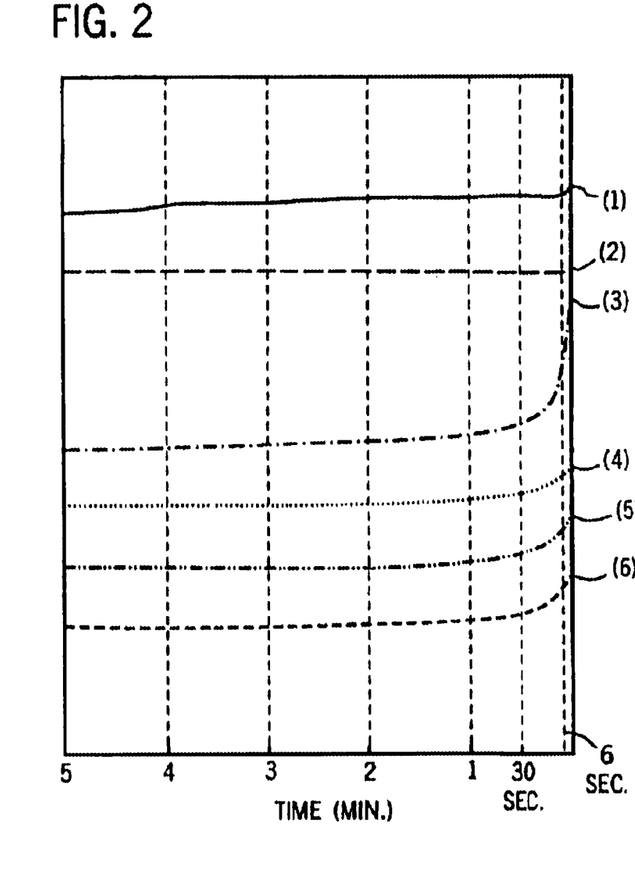
FIG. 2 is a series of absorbance curves plotted versus time to demonstrate the time to chromogen formation and chromogen stability for various reagents, including the lysing reagent of the present invention.

In order to show the desirability of the present invention as an alternative to the cyanide-containing reagents currently in use, it is necessary to demonstrate that the lysing agent of the present invention had comparable performance characteristics to those reagents which it is to replace. FIG. 2 is a summary of experiments which were conducted to evaluate the reaction times (the conversion rate of hemoglobin at peak performance) and the stability of various prior art reagents and of the lysing reagent of the present invention at 540 nm. Reaction time is important to the performance of this reagent on hematology instruments especially in manual and semi-automated instruments. The timing of the readings in such instruments could affect the results. Therefore, a fast reacting lyse reagent and a fast forming, stable chromogen can help alleviate problems with timing. Similarly, chromogen stability after formation is essential to the use of this reagent on automated and semi-automated instruments. FIG. 2 indicates that the lysing reagent of the present invention experiences rapid chromogen formation followed by very stable absorbance characteristics. Both of these characteristics were significantly better for the lysing reagent of the present invention than for the prior art cyanide-free reagents (curves 3, 4, 5 and 6). While the reference method with cyanide had a greater absorbance value, the cyanide-free reagent of the present method exhibits more rapid reaction time and greater chromogen stability.

Figure 3:
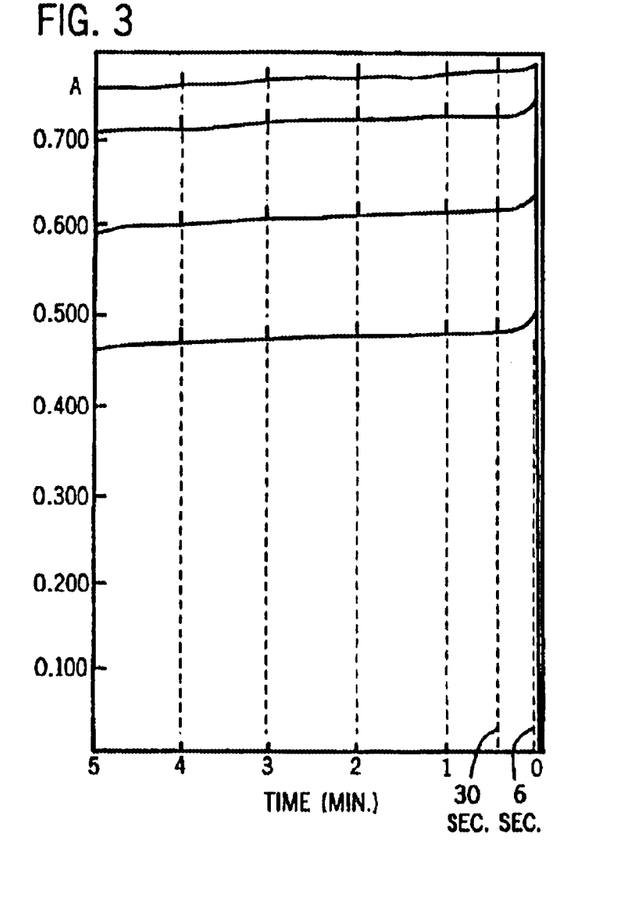
FIG. 3 is another series of absorbance curves for various hemoglobin concentrations plotted against time to show reaction rates and stability for the selected current reference method.
Figure 4:
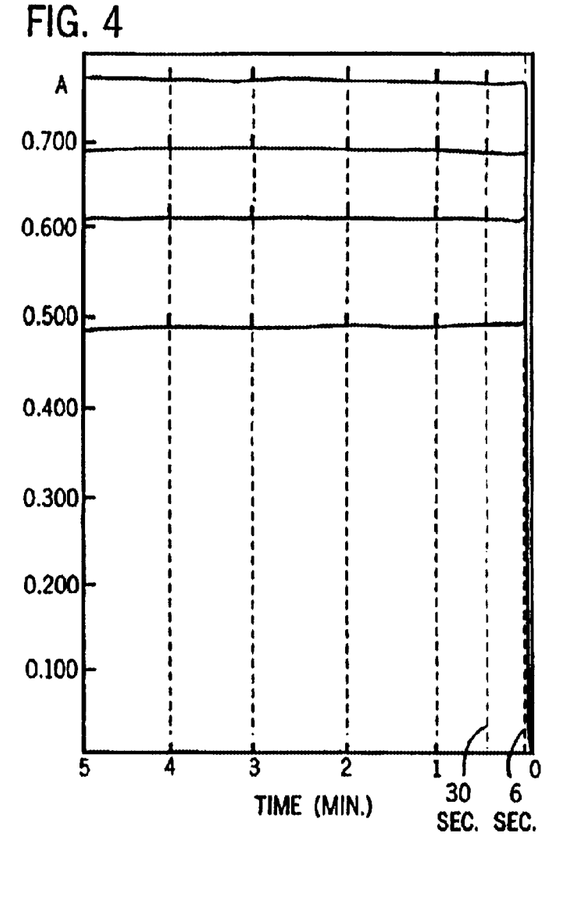
FIG. 4 is a series of absorbance curves plotted against time to show reaction rates and stability for various concentrations of hemoglobin (same as in FIG. 3) using the method of the present invention.

FIG. 3 shows chromogen formation time and chromogen stability over time for blood samples with various hemoglobin concentrations (from bottom to top, 7.7 grams/ deciliter (g/dL), 12.3 g/dL, 16.5 g/dL and 21.5 g/dL) with a reference lyse containing cyanide. FIG. 4 shows chromogen formation time and chromogen stability over time for blood samples at these same hemoglobin concentrations, but instead using the lysing reagent of the present invention. A comparison of these two figures suggests that the reagent of the present invention demonstrates more rapid and more stable chromogen formation across the entire clinical range of hemoglobin concentrations in whole blood samples.

The present invention will now be described with reference to examples which are intended to illustrate the scope and compatibility of the present invention with current standard methods and instrumentations. These examples are not intended to limit the scope of the present invention.

The following are the compositional ingredients of the diluents of the present invention:

Diluent No. 1:
   Sodium Phosphate, Sodium Chloride, Sodium Fluoride, Potassium Chloride, Ethylenediaminetetraacetic Acid (EDTA), and Phenoxyethanol.

Diluent No. 2:
   Sodium Sulfate, Sodium Chloride, EDTA, Imidazole, and Triadine-10 (a mixture of hexahydro-1,3,5-tris(2-hydroxyethyl)-s-triazine and sodium 2-pyridinethiol-1-oxide).

Diluent No. 3:
   Sodium Sulfate, Sodium Chloride, EDTA, Imidazole, Triadine-10 (a mixture of hexahydro-1,3,5-tris(2-hydroxyethyl)-s-triazine and sodium 2-pyridinethiol-1-oxide), and Polyethylene Glycol.

The following are the compositional examples of the lysing reagent of the present invention.

| Formula No. 1: | |
|---|---|
| alkyltrimethylammonium salts, alkyldimethylbenzylammonium salts or alkylpyridium salts [tetradecyltrimethyl ammonium bromide (TTAB), dodecyltrimethyl ammonium chloride, cetyltrimethyl ammonium bromide, hexadecyltrimethyl ammonium bromide and benzalkonium chlorides] | 10–20% (wt) |
| hydroxylamine hydrochloride | 2–15% (wt) |
| deionized water | 65–88% (wt) |

| Formula No. 2: | |
|---|---|
| benzalkonium chloride | 2–10% (wt) |
| dodecyltrimethyl ammonium chloride | 2–10% (wt) |
| hydroxylamine hydrochloride | 1–5% (wt) |
| deionized water | 75–95% (wt) |

| Formula No. 3: | |
|---|---|
| tetradecyltrimethylammonium bromide (TTAB) | 0–1% (wt) |
| dodecyltrimethylammonium chloride | 2–10% (wt) |
| hydroxylamine hydrochloride | 0.1–1% (wt) |
| deionized water | 88–97.9% (wt) |

| Formula No. 4: | |
|---|---|
| benzalkonium chloride | 0.1–5% (wt) |
| dodecyltrimethyl ammonium chloride | 0.1–5% (wt) |
| hydroxylamine hydrochloride | 0.1–1% (wt) |
| deionized water | 89–99.7% (wt) |

For Examples 1–18, and 20 the diluent used was Diluent No. 2. In Example 19 the diluent used was Diluent No. 1. Example 21 utilized Diluent No. 3. In all the Examples except as otherwise noted, thirty (30) microliters (μL) of whole blood was prediluted with 7.5 milliliters (mL) of diluent to give a 1:250 dilution. One (1) mL of a multipurpose lysing reagent was added to the diluted whole blood sample.

Salts such as sodium chloride (NaCl), potassium chloride (KCl) and the like may be added to increase the conductivity of the liquid reagents utilized in instruments. The increased conductivity can be used for sensor detection of low liquid levels in reagent containers.

EXAMPLE 1

A multipurpose lysing reagent was prepared by dissolving 20 grams (g) of hydroxylamine hydrochloride (Sigma, St. Louis, Mo., 63178), 37.5 g of benzalkonium chloride (Amresco, Solon, Ohio., 44139) and 37.5 g dodecyltrimethyl ammonium chloride (Sigma) in 1 liter of deionized water. Alternatively, 42.5 g of benzalkonium chloride and 42.5 g of dodecyltrimethyl ammonium chloride can be used. The results displayed in Table 1 utilize 37.5 g of both quarternary ammonium salts in the aqueous lyse reagent. This lysing reagent can be used in the Cell-Dyn® 1300, 1600 and 3500 instruments. A serial concentration of whole blood was analyzed for hemoglobin content in the Abbott Diagnostics Cell-Dyn® Model 1600 according to the standard operating procedures to investigate the correlation of the results obtained with the cyanide-containing reference lyse (Cell-Dyn® Rapid Lyse) and with the multipurpose (CN-free) lysing reagent of the present invention. Data are presented in Table 1.

TABLE 1

| Reference Lyse (g/dL) | Experimental Lyse (g/dL) |
|---|---|
| 3.3 | 3.4 |
| 4.7 | 4.9 |
| 8.3 | 8.4 |
| 9.8 | 10.1 |
| 10.1 | 10.3 |
| 13.1 | 13.4 |
| 13.6 | 13.7 |
| 14.6 | 14.9 |
| 15.2 | 15.5 |
| 17.4 | 17.6 |
| 19.2 | 19.2 |
| 19.5 | 19.7 |
| 23.1 | 23.2 |
| 24.0 | 23.9 |
| 29.1 | 29.0 |

The reported hemoglobin values are the mean of two assays for prepared fresh blood. The correlation parameters for this data are n=15, r=0.999, y=0.297+0.990 x, X=15, Y=15.15, indicating a high level of correlation between the data for the reference and experimental reagents.

EXAMPLE 2

Using the experimental lysing reagent prepared in Example 1, a serial concentration of prepared whole blood was analyzed for white blood cell counts (WBC) in the Cell-Dyn® 1600 instrument with the reference lyse (Cell-Dyn® Rapid Lyse) and the experimental lyse. The blood samples contained platelets <666 K/μL (K=1000x) and hemoglobin <18.6 g/dL. The WBC results are reported in Table 2.

TABLE 2

| Reference Lyse WBC (K/μL) | Experimental Lyse WBC (K/μL) |
|---|---|
| 3.1 | 3.0 |
| 6.5 | 6.3 |
| 6.7 | 6.9 |
| 8.5 | 8.6 |
| 16.8 | 16.5 |
| 25.4 | 25.7 |
| 50.5 | 51.3 |
| 67.8 | 67.6 |
| 76.2 | 77.3 |
| 100.9 | 102.5 |

The reported hemoglobin values are the mean of two assays for prepared fresh blood. The correlation parameters for this data are n=10, r=0.999, y=0.178+1.014 x, X=36.24, Y=36.57, indicating a high level of correlation between the data for the two reagents.

EXAMPLE 3

An experimental lysing reagent prepared according to the formulation set forth in Example 1 was used to compare the reproducibility of the experimental lyse versus the Cell-Dyn® Rapid Lyse used as a reference lyse. Three fresh blood samples were analyzed with the two lysing reagents on the Cell-Dyn® 1600 instrument. The results are set out below in Tables 3 and 4. Table 5 shows good correlation between two lyse reagents for Hb and WBC determinations.

TABLE 3

CELL-DYN® 1600 RAPID LYSE REFERENCE

| | Sample #1 | | Sample #2 | | Sample #3 | |
|---|---|---|---|---|---|---|
| RUN NO. | Hb (g/dL) | WBC (K/μL) | Hb (g/dL) | WBC (K/μL) | Hb (g/dL) | WBC (K/μL) |
| 1 | 3.2 | 4.2 | 14.5 | 5.4 | 22.9 | 6 |
| 2 | 3.3 | 4.3 | 14.6 | 5.3 | 23.2 | 6.2 |
| 3 | 3.2 | 4.3 | 14.6 | 5.2 | 23.3 | 6.2 |
| 4 | 3.3 | 4.3 | 14.7 | 5.4 | N/A* | N/A |
| 5 | 3.3 | 4.3 | 14.8 | 5.4 | N/A | N/A |
| 6 | 3.3 | 4.3 | 14.7 | 5.5 | N/A | N/A |
| 7 | 3.3 | 4.2 | 14.8 | 5.2 | N/A | N/A |
| 8 | 3.3 | 4.5 | 14.6 | 5.4 | N/A | N/A |
| 9 | 3.3 | 4.4 | 14.8 | 5.4 | N/A | N/A |
| 10 | 3.3 | 4.3 | 14.8 | 5.5 | N/A | N/A |
| Mean | 3.3 | 4.3 | 14.7 | 5.4 | 23.2 | 6.1 |
| SD | 0.0 | 0.1 | 0.1 | 0.1 | 0.2 | 0.1 |
| CV | 1.2 | 2 | 0.7 | 1.9 | 0.8 | 1.5 |

*Insufficient sample volume available.

TABLE 4

CELL-DYN® 1600 EXAMPLE 1 CN-FREE LYSE

| | Sample #1 | | Sample #2 | | Sample #3 | |
|---|---|---|---|---|---|---|
| RUN NO. | Hb (g/dL) | WBC (K/μL) | Hb (g/dL) | WBC (K/μL) | Hb (g/dL) | WBC (K/μL) |
| 1 | 3.3 | 4.3 | 14.6 | 5.3 | 23.4 | 6.1 |
| 2 | 3.3 | 4.5 | 14.6 | 5.5 | 23.5 | 6.1 |
| 3 | 3.4 | 4.4 | 14.5 | 5.3 | 23.4 | 6.2 |
| 4 | 3.4 | 4.6 | 14.6 | 5.6 | 23.2 | 6.1 |
| 5 | 3.3 | 4.4 | 14.6 | 5.4 | 23.3 | 6.3 |
| 6 | 3.4 | 4.5 | 14.7 | 5.5 | 23.5 | 6.5 |
| 7 | 3.3 | 4.6 | 14.7 | 5.6 | 23.2 | 6.1 |
| 8 | 3.4 | 4.5 | 14.6 | 5.5 | 23.5 | 6.4 |

TABLE 4-continued

CELL-DYN® 1600 EXAMPLE 1 CN-FREE LYSE

| | Sample #1 | | Sample #2 | | Sample #3 | |
|---|---|---|---|---|---|---|
| RUN NO. | Hb (g/dL) | WBC (K/μL) | Hb (g/dL) | WBC (K/μL) | Hb (g/dL) | WBC (K/μL) |
| 9 | 3.3 | 4.5 | 14.7 | 5.6 | 23.5 | 6.3 |
| 10 | 3.4 | 4.4 | 14.5 | 5.5 | 23.2 | 6.3 |
| Mean | 3.4 | 4.5 | 14.6 | 5.5 | 23.4 | 6.2 |
| SD | 0.1 | 0.1 | 0.1 | 0.1 | 0.1 | 0.1 |
| CV | 1.5 | 2.1 | 0.5 | 2 | 0.5 | 2.2 |

TABLE 5

| PARAMETER* | LOW ABNORMAL | ABSOLUTE WITHIN SAMPLE |
|---|---|---|
| WBC (K/μL) | 0.5–4.6 | 14.6–10.2 |
| | SD <0.2 | CV <2.5% |
| Hb (g/dL) | Below 12.2 | 12.2–18.1 |
| | SD <0.2 | CV <1.2% |

*The values in Table 4 were compared to the precision specifications for the instrument at 25° C.

Overall there was good correlation in both sets of data for the two parameters observed.

EXAMPLE 4

Using the experimental lysing reagent prepared in Example 1, whole blood was analyzed for hemoglobin in the Cell-Dyn® 1600 instrument with the reference lyse (Cell-Dyn® Rapid Lyse) and the experimental lyse. The hemoglobin results are reported in Table 6.

TABLE 6

| Sample | Reference Lyse Hb (g/dL) | Experimental Lyse Hb (g/dL) | Sample | Reference Lyse Hb (g/dL) | Experimental Lyse Hb (g/dL) |
|---|---|---|---|---|---|
| 1 | 15.3 | 15.2 | 32 | 14.6 | 14.9 |
| 2 | 15.8 | 15.7 | 33 | 17.4 | 17.6 |
| 3 | 13.3 | 13.4 | 34 | 23.1 | 23.2 |
| 4 | 16.9 | 16.9 | 35 | 29.1 | 29.0 |
| 5 | 13.8 | 13.9 | 36 | 14.4 | 14.7 |
| 6 | 12.8 | 12.7 | 37 | 14.8 | 15.0 |
| 7 | 15.7 | 15.7 | 38 | 14.5 | 14.9 |
| 8 | 15.6 | 15.5 | 39 | 15.1 | 15.1 |
| 9 | 14.6 | 14.5 | 40 | 16.4 | 16.2 |
| 10 | 13.7 | 13.6 | 41 | 13.6 | 13.7 |
| 11 | 15.4 | 15.4 | 42 | 7.7 | 7.8 |
| 12 | 14.1 | 14.2 | 43 | 12.3 | 12.4 |
| 13 | 13.4 | 13.6 | 44 | 16.5 | 16.6 |
| 14 | 15.3 | 15.2 | 45 | 21.5 | 21.8 |
| 15 | 13.9 | 13.9 | 46 | 3.3 | 3.3 |
| 16 | 12.7 | 13.0 | 47 | 14.7 | 14.6 |
| 17 | 14.1 | 14.1 | 48 | 23.2 | 23.4 |
| 18 | 14.5 | 14.4 | 49 | 15.3 | 15.3 |
| 19 | 13.6 | 13.7 | 50 | 15.0 | 14.8 |
| 20 | 19.2 | 19.2 | 51 | 12.3 | 12.2 |
| 21 | 8.3 | 8.4 | 52 | 14.4 | 14.3 |
| 22 | 15.1 | 15.5 | 53 | 14.3 | 14.1 |
| 23 | 19.5 | 19.7 | 54 | 15.2 | 15.1 |
| 24 | 10.1 | 10.3 | 55 | 14.2 | 14.3 |
| 25 | 13.1 | 13.4 | 56 | 13.8 | 13.8 |
| 26 | 24.0 | 23.9 | 57 | 16.4 | 16.2 |
| 27 | 9.8 | 10.1 | 58 | 14.0 | 13.9 |
| 28 | 13.0 | 13.2 | 59 | 13.2 | 13.1 |
| 29 | 14.7 | 14.8 | 60 | 16.2 | 16.3 |
| 30 | 15.1 | 15.1 | 61 | 12.5 | 12.4 |
| 31 | 4.7 | 4.9 | 62 | 13.3 | 13.1 |

The correlation parameters for this data are n=62, r=0.999, y=0.106+0.996 x, X=14.73, Y=14.78, indicating a high level of correlation between the data for the two reagents.

EXAMPLE 5

Using the experimental lysing reagent prepared in Example 1, whole blood was analyzed for WBC counts in the Cell-Dyn® 1600 instrument with the reference lyse (Cell-Dyn® Rapid Lyse) and the experimental lyse. The WBC results are reported in Table 7.

TABLE 7

| Sample | Reference Lyse WBC (K/μL) | Experimental Lyse WBC (K/μL) | Sample | Reference Lyse WBC (K/μL) | Experimental Lyse WBC (K/μL) |
|---|---|---|---|---|---|
| 1 | 100.9 | 102.5 | 32 | 4.3 | 4.4 |
| 2 | 76.2 | 77.3 | 33 | 6.7 | 6.9 |
| 3 | 50.5 | 51.3 | 34 | 6.0 | 6.0 |
| 4 | 25.4 | 25.7 | 35 | 6.8 | 6.8 |
| 5 | 6.7 | 6.9 | 36 | 3.5 | 3.4 |
| 6 | 27.4 | 28.4 | 37 | 6.7 | 6.9 |
| 7 | 29.0 | 29.3 | 38 | 16.8 | 16.5 |
| 8 | 12.5 | 12.5 | 39 | 67.8 | 67.6 |
| 9 | 6.6 | 6.6 | 40 | 6.4 | 6.6 |
| 10 | 4.9 | 4.9 | 41 | 5.7 | 5.7 |
| 11 | 8.9 | 8.8 | 42 | 3.4 | 3.5 |
| 12 | 7.0 | 6.8 | 43 | 4.6 | 4.4 |
| 13 | 8.6 | 8.3 | 44 | 6.7 | 6.6 |
| 14 | 3.3 | 3.3 | 45 | 9.3 | 9.2 |
| 15 | 6.0 | 5.9 | 46 | 4.3 | 4.5 |
| 16 | 10.3 | 10.3 | 47 | 5.4 | 5.5 |
| 17 | 4.2 | 4.2 | 48 | 6.1 | 6.3 |
| 18 | 5.3 | 5.4 | 49 | 4.3 | 4.2 |
| 19 | 5.8 | 5.7 | 50 | 6.6 | 6.5 |
| 20 | 4.9 | 5.0 | 51 | 4.7 | 4.8 |
| 21 | 5.7 | 5.7 | 52 | 7.3 | 7.4 |
| 22 | 4.6 | 4.6 | 53 | 6.1 | 6.0 |
| 23 | 6.0 | 6.0 | 54 | 3.1 | 3.0 |
| 24 | 9.3 | 9.1 | 55 | 6.9 | 6.8 |
| 25 | 4.0 | 3.9 | 56 | 8.5 | 8.6 |
| 26 | 5.7 | 5.7 | 57 | 7.8 | 7.7 |
| 27 | 6.9 | 7.0 | 58 | 4.2 | 4.2 |
| 28 | 3.6 | 3.7 | 59 | 8.4 | 8.3 |
| 29 | 4.8 | 4.8 | 60 | 4.0 | 4.4 |
| 30 | 8.5 | 8.3 | 61 | 7.0 | 7.3 |
| 31 | 5.7 | 5.4 | 62 | 5.9 | 6.1 |

The correlation parameters for this data are n=62, r=0.999, y=0.081+1.013 x, X=11.68, Y=11.75, indicating a high level of correlation between the data for the two reagents.

EXAMPLE 6

Using the experimental lysing reagent prepared according to Example 1 and the reference lyse (Cell-Dyn® Rapid Lyse), hemoglobin content was assayed in the Cell-Dyn® 1600 in the presence of serial WBC concentrations. The purpose of this study was to determine whether there was any significant interference on hemoglobin values when blood samples having high WBC counts are analyzed. The permissible quality control limits for hemoglobin and WBC are ±0.3 units or 3% whichever is greater. The results presented in Table 8 indicate that the experimental lyse is very comparable to the reference lyse with no significant difference between the two reagents due to high WBC counts.

TABLE 8

| | Blood A | | Blood B | | Blood C | | Blood D | | Blood E | |
|---|---|---|---|---|---|---|---|---|---|---|
| | Hb g/dL | WBC K/μL | Hb g/dL | WBC K/μL | Hb g/dL | WBC K/μL | Hb g/dL | WBC K/μL | Hb g/dL | WBC K/μL |
| Reference Lyse | 14.3 | 6.7 | 13.8 | 25.4 | 13.9 | 50.5 | 14.2 | 76.2 | 14.3 | 101* |
| Experimental Lyse | 14.5 | 6.9 | 14.1 | 25.7 | 14.3 | 51.3 | 14.3 | 77.3 | 14.8 | 102* |

*Based upon count for 50% dilution.

EXAMPLE 7

Using the experimental lysing reagent prepared according to Example 1 and the reference lyse (Cell-Dyn® Rapid Lyse), hemoglobin and platelet counts were performed using the Cell-Dyn® 1600 with serial platelet (PLT) concentrations. The purpose of this study was to determine whether there was any significant interference when blood samples having high number of platelets are analyzed. The permissible quality control limits for hemoglobin are ±0.3 units or 3% which ever is greater. The results presented in Table 9 do not reveal any significant level of difference between the two reagents due to high platelet numbers.

TABLE 9

| | Blood A | | Blood B | | Blood C | | Blood D | | Blood E | |
|---|---|---|---|---|---|---|---|---|---|---|
| | Hb g/dL | PLT K/μL | Hb g/dL | PLT K/μL | Hb g/dL | PLT K/μL | Hb g/dL | PLT K/μL | Hb g/dL | PLT K/μL |
| Reference Lyse | 14.3 | 302 | 13.8 | 495 | 13.9 | 573 | 10.4 | 905 | 11.7 | 1040* |
| Experimental Lyse | 14.5 | 308 | 14.1 | 514 | 14.3 | 564 | 10.8 | 902 | 12.1 | 1070 |

*Based upon count for 50% dilution.

EXAMPLE 8

Using the experimental lysing reagent prepared according to Example 1 and the reference lyse (Cell-Dyn® Rapid Lyse), hemoglobin and WBC counts were performed using the Cell-Dyn® 1600 with serial lipid/lipoprotein concentrations. The purpose of this study was to determine the effect of increased sample turbidity by lipid/lipoproteins (Sigma/L-5401) on hemoglobin and WBC determinations. The results presented in Table 10 do not demonstrate significant difference between the two reagents.

TABLE 10

|  | Blood A 0.107 OD* | | Blood B 0.621 OD* | | Blood C 1.165 OD* | | Blood D 1.698 OD* | |
| --- | --- | --- | --- | --- | --- | --- | --- | --- |
|  | Hb g/dL | WBC K/µL | Hb g/dL | WBC K/µL | Hb g/dL | WBC K/µL | Hb g/dL | WBC K/µL |
| Reference Lyse | 15.5 | 6.3 | 16.0 | 6.6 | 15.5 | 7.5 | 15.2 | 7.3 |
| Experimental Lyse | 15.4 | 6.2 | 16.1 | 6.6 | 15.7 | 7.2 | 15.5 | 7.4 |

*OD = Optical density of supernatant after centrifugation.

EXAMPLE 9

Using the experimental lysing reagent prepared according to Example 1 and the reference lyse (Cell-Dyn® Rapid Lyse), hemoglobin and WBC counts were performed using the Cell-Dyn® 1600 with serial lipid/lipoprotein concentrations. The samples were also analyzed with the Coulter® S-Plus STKR System (Coulter Corp., Hialeah, Fla.,33012). The purpose of this study was to determine the effect of increased sample turbidity by different sources of lipid/lipoproteins from Intralipos (Green Cross, Japan) on hemoglobin and WBC determinations. The results presented in Table 11 do not reveal any significant difference between the three reagents.

TABLE 11

| | Mean of Hb | | | | | | | |
| --- | --- | --- | --- | --- | --- | --- | --- | --- |
|  | Blood A 0.48 OD* | | Blood B 1.52 OD* | | Blood C 1.643 OD* | | Blood D 1.678 OD* | |
|  | Hb g/dL | WBC K/µL | Hb g/dL | WBC K/µL | Hb g/dL | WBC K/µL | Hb g/dL | WBC K/µL |
| Reference Lyse | 14.3 | 8.3 | 15.3 | 8.2 | 17.6 | 8.0 | 21.1 | 40.2 |
| Experimental Lyse | 14.4 | 8.2 | 15.4 | 8.3 | 17.9 | 8.0 | 21.5 | 39.6 |
| Coulter's** STKR | 14.9 | 9.1 | 15.4 | 8.7 | 17.7 | 8.4 | 20.6 | 44.0 |

*OD = Optical density of supernatant after centrifugation.
**No cross calibration between Cell Dyn® 1600 and Coulter® STKR System.

EXAMPLE 10

Using the experimental lysing reagent prepared according to Example 1 and the reference lyse (Cell-Dyn® Rapid Lyse), hemoglobin and WBC counts were performed using the Cell-Dyn® 1600. Different levels of bilirubin (0.25% DMSO solution) were added to blood samples. The purpose of this study was to determine the effect of bilirubin on hemoglobin and WBC determinations. The results presented in Table 12 do not reveal any significant difference between the two reagents.

TABLE 12

|  | Blood A Bilirubin (Blank) | | Blood B Bilirubin (10 mg/dL) | | Blood C Bilirubin (20 mg/dL) | | Blood D Bilirubin (30 mg/dL) | |
| --- | --- | --- | --- | --- | --- | --- | --- | --- |
|  | Hb g/dL | WBC K/µL | Hb g/dL | WBC K/µL | Hb g/dL | WBC K/µL | Hb g/dL | WBC K/µL |
| Reference Lyse | 14.3 | 5.2 | 14.2 | 5.2 | 14.1 | 5.1 | 13.8 | 5.0 |
| Experimental Lyse | 14.2 | 5.2 | 14.3 | 5.1 | 14.3 | 5.2 | 14.1 | 5.1 |

EXAMPLE 11

Using the experimental lysing reagent prepared according to Example 1 and the reference lyse (Cell-Dyn® Rapid Lyse), hemoglobin and WBC counts were performed using the Cell-Dyn® 1600. Different levels of methemoglobin were obtained by adding sodium nitrite solutions with different concentrations to the blood samples. It is known that methemoglobin can effect some methods of hemoglobin determination. The purpose of this study was to determine the effect of methemoglobin on hemoglobin and on WBC determinations with CN-free reagent. The results presented in Table 13 indicate that there are no significant differences between the two reagents.

TABLE 13

|  | Blood A $N_aNO_2$ (Blank) | | Blood B NaN02 (20 mg) | | Blood C NaN02 (50 mg) | | Blood D NaN02 (100 mg) | | Blood E NaN02 (200 mg) | |
| --- | --- | --- | --- | --- | --- | --- | --- | --- | --- | --- |
|  | Hb g/dL | WBC K/μL | Hb g/dL | WBC K/μL | Hb g/dL | WBC K/μL | Hb g/dL | WBC K/μL | Hb g/dL | WBC K/μL |
| Reference Lyse | 13.0 | 8.0 | 13.1 | 8.1 | 13.0 | 8.1 | 13.1 | 8.0 | 13.3 | 7.9 |
| Experimental Lyse | 13.1 | 8.0 | 13.0 | 8.0 | 13.1 | 8.0 | 13.4 | 8.1 | 13.2 | 7.9 |

EXAMPLE 12

Using the experimental lysing reagent prepared according to Example 1 and the reference lyse (Cell-Dyn® Rapid Lyse), hemoglobin and WBC counts were performed using the Cell-Dyn® 1600. Carboxyhemoglobin is also known to effect the performance of some hemoglobin methods. Different levels of carboxyhemoglobin were studied using the Dade Quantra Plus Whole Blood Gas Controls (Baxter Diagnostics, Inc., Deerfield, Ill., 60015), and Cell-Dyn® 16 hematology whole blood controls (Low, Normal and High) for a comparison study with the two reagents in the Cell-Dyn® 1600. The IL-282 CO Oximeter results were listed in the control insert sheets.

The purpose of this study was to determine the effect of carboxyhemoglobin on hemoglobin determination with CN-free reagent. The results presented in Table 14 do not reveal any significant differences between the two reagents.

EXAMPLE 13

Using the experimental lysing reagent prepared according to Example 1 and the reference lyse (Cell-Dyn® Rapid Lyse), hemoglobin and WBC counts were performed using the Cell-Dyn® 1600. The purpose of this test was to evaluate the real time stability of the experimental lyse. The results reported in Table 15 demonstrate that the experimental lyse is stable at room temperature over time.

TABLE 14

|  | Dade Quantra (%) HbCO | | | | | | Cell-Dyn Control | | |
| --- | --- | --- | --- | --- | --- | --- | --- | --- | --- |
|  | QI | | QII | | QIII | | | | |
|  | (A) 13.7% | (B) 16.4% | (A) 3.3% Hb (g/dL) | (B) 3.7% | (A) 39.9% | (B) 40.8% | Low 7.8 ± 0.3 | Norm 13 ± 0.4 Hb (g/dL) | High 16.8 ± 0.5 |
| Reference Lyse | 9.4 | 9.2 | 12.8 | 13.0 | 14.5 | 15.0 | 7.5 | 12.8 | 16.5 |
| Experimental Lyse | 9.2 | 9.2 | 13.1 | 13.0 | 14.3 | 14.9 | 7.8 | 13.0 | 16.5 |
| IL-282 Co-Oximeter* | 9.7 | 9.4 | 13.4 | 13.5 | 14.6 | 14.9 | — | — | — |

*Carboxyhemoglobin values listed (as a percentage in Table 14) and IL-282 Co-Oximeter values obtained from the control insert sheets.
(A), QI = Level (I) Acidosis (Lot #BG01-268).
(A), QII = Level (II) Normal (Lot #BG02-276).
(A), QIII = Level (III) Alkalosis (Lot #BG03-285).
(B), QI = Level (I) Acidosis (Lot #BG01-276).
(B), QII = Level (II) Normal (Lot #BG02-284).
(B), QIII = Level (III) Alkalosis (Lot #BG03-293).

TABLE 15

| CD-1600 METHOD/LYSE | FRESH BLOOD | | | | | | | | | | | | | | | |
|---|---|---|---|---|---|---|---|---|---|---|---|---|---|---|---|---|
| | 1 | | 2 | | 3 | | 4 | | 5 | | 6 | | 7 | | 8 | |
| | Hb g/dL | WBC K/μL | Hb g/dL | WBC K/μL | Hb g/dL | WBC K/μL | Hb g/dL | WBC K/μL | Hb g/dL | WBC K/μL | Hb g/dL | WBC K/μL | Hb g/dL | WBC K/μL | Hb g/dL | WBC K/μL |
| Reference Lyse (CN) 405 (Current) | 15.4 | 10.3 | 14.1 | 4.2 | 13.4 | 5.3 | 15.3 | 5.8 | 14.1 | 5 | 13 | 5.8 | 14.5 | 4.7 | 14.5 | 6 |
| Experimental Lyse (CN-Free) (3 Months) | 15.4 | 10.3 | 14.2 | 4.2 | 13.6 | 5.4 | 15.2 | 5.7 | — | — | — | — | — | — | — | — |
| Experimental Lyse (CN-Free) (4 Months) | — | — | — | — | — | — | — | — | 14.2 | 4.9 | 13.1 | 5.8 | 14.5 | 4.7 | 14.6 | 6.1 |
| Experimental Lyse (CN-Free) (5 Months) | — | — | — | — | — | — | — | — | — | — | — | — | — | — | — | — |
| Experimental Lyse (CN-Free) (6 Months) | 15.3 | 10.2 | 14.3 | 4.3 | 13.7 | 5.3 | 15.4 | 5.8 | — | — | — | | — | — | — | — |
| Experimental Lyse (CN-Free) (7 Months) | — | — | — | — | — | — | — | — | 13.9 | 5 | 13.1 | 5.7 | 14.3 | 4.6 | 14.5 | 6 |
| Experimental Lyse (CN-Free) (8 Months) | — | — | — | — | — | — | — | — | — | — | — | — | — | — | — | — |
| Experimental Lyse (CN-Free) (9 Months) | — | — | — | — | — | — | — | — | — | — | — | — | — | — | — | — |
| Experimental Lyse (CN-Free) (13 Months) | 15.4 | 10.3 | 14.2 | 4.2 | 13.5 | 5.3 | 15.3 | 5.8 | — | — | — | — | — | — | — | — |
| Experimental Lyse (CN-Free) (14 Months) | — | — | — | — | — | — | — | — | — | — | — | — | — | — | — | — |
| Experimental Lyse (CN-Free) (15 Months) | — | — | — | — | — | — | — | — | — | — | — | — | — | — | — | — |
| Experimental Lyse (CN-Free) (16 Months) | 15.6 | 10.4 | 14.4 | 4.2 | 13.6 | 5.1 | 15.2 | 5.8 | — | — | — | — | — | — | — | — |
| Experimental Lyse (CN-Free) (17 Months) | — | — | — | — | — | — | — | — | — | — | — | — | — | — | — | — |
| Experimental Lyse (CN-Free) (18 Months) | — | — | — | — | — | — | — | — | — | — | — | — | — | — | — | — |
| Experimental Lyse (CN-Free) (20 Months) | — | — | — | — | — | — | — | — | — | — | — | — | — | — | — | — |

| CD-1600 METHOD/LYSE | FRESH BLOOD | | | | | | | | | | | |
|---|---|---|---|---|---|---|---|---|---|---|---|---|
| | 9 | | 10 | | 11 | | 12 | | 13 | | 14 | |
| | Hb g/dL | WBC K/μL | Hb g/dL | WBC K/μL | Hb g/dL | WBC K/μL | Hb g/dL | WBC K/μL | Hb g/dL | WBC K/μL | Hb g/dL | WBC K/μL |
| Reference Lyse (CN) 405 (Current) | 16.9 | 8.9 | 13.8 | 7 | 12.8 | 8.6 | 15.7 | 5.8 | 15.6 | 3.3 | 14.6 | 6 |
| Experimental Lyse (CN-Free) (3 Months) | — | — | — | — | — | — | — | — | — | — | — | — |
| Experimental Lyse (CN-Free) (4 Months) | — | — | — | — | — | — | — | — | — | — | — | — |
| Experimental Lyse (CN-Free) (5 Months) | 16.9 | 8.8 | 13.9 | 6.8 | 12.7 | 8.3 | — | — | — | — | — | — |
| Experimental Lyse (CN-Free) (6 Months) | — | — | — | — | — | — | 15.7 | 5.6 | 15.5 | 3.3 | 14.5 | 5.9 |
| Experimental Lyse (CN-Free) (7 Months) | — | — | — | — | — | — | — | — | — | — | — | — |
| Experimental Lyse (CN-Free) (8 Months) | 16.8 | 8.8 | 14 | 7 | 13.1 | 8.7 | — | — | — | — | — | — |
| Experimental Lyse (CN-Free) (9 Months) | — | — | — | — | — | — | 15.5 | 5.6 | 15.7 | 3.3 | 14.7 | 5.9 |
| Experimental Lyse (CN-Free) (13 Months) | — | — | — | — | — | — | — | — | — | — | — | — |
| Experimental Lyse (CN-Free) (14 Months) | 16.9 | 8.6 | 14 | 6.9 | 13 | 8.5 | — | — | — | — | — | — |
| Experimental Lyse (CN-Free) (15 Months) | 16.9 | 8.6 | 13.8 | 6.9 | 12.8 | 8.4 | — | — | — | — | — | — |
| Experimental Lyse (CN-Free) (16 Months) | — | — | — | — | — | — | — | — | — | — | — | — |
| Experimental Lyse (CN-Free) (17 Months) | 17 | 8.8 | 14 | 7.1 | 13.1 | 8.4 | — | — | — | — | — | — |
| Experimental Lyse (CN-Free) (18 Months) | — | — | — | — | — | — | 13.3 | 5.7 | 13.0 | 6.9 | 13.7 | 7.8 |
| Experimental Lyse (CN-Free) (20 Months) | — | — | — | — | — | — | 13.1 | 5.6 | 12.9 | 6.7 | 13.9 | 7.9 |

EXAMPLE 14

Using the experimental lyse prepared according to Example 1 and the reference lyse (Cell-Dyn® Rapid Lye), hemoglobin and WBC counts were performed using the Cell-Dyn® 1600. The purpose of this test was to evaluate the stability of the experimental lyse in a temperature stressed condition. The results reported in Table 16 demonstrates that the experimental lyse, stressed at both 60° C. and room temperature for fifteen months still maintains comparable performances to the reference lyse.

TABLE 16

| CD-1600 | FRESH BLOOD | | | | | | | | | | | | | | | |
|---|---|---|---|---|---|---|---|---|---|---|---|---|---|---|---|---|
| | 1 | | 2 | | 3 | | 4 | | 5 | | 6 | | 7 | | 8 | |
| METHOD/LYSE (TIME/TEMP.) | Hb g/dL | WBC K/μL | Hb g/dL | WBC K/μL | Hb g/dL | WBC K/μL | Hb g/dL | WBC K/μL | Hb g/dL | WBC K/μL | Hb g/dL | WBC K/μL | Hb g/dL | WBC K/μL | Hb g/dL | WBC K/μL |
| Reference Lyse (CN) 405 (Current/Room Temperature) | 15.4 | 10.3 | 14.1 | 4.2 | 13.4 | 5.3 | 15.3 | 5.8 | 14.1 | 5 | 13 | 5.8 | 14.5 | 4.7 | 14.5 | 6 |
| Experimental Lyse (CN-Free) (3 Mos./Room Temperature) | 15.4 | 10.3 | 14.2 | 4.2 | 13.6 | 5.4 | 15.2 | 5.7 | — | — | — | — | — | — | — | — |
| Experimental Lyse (CN-Free) (4 Mos./Room Temperature) | — | — | — | — | — | — | — | — | 14.2 | 4.9 | 13.1 | 5.8 | 14.5 | 4.7 | 14.6 | 6.1 |
| Experimental Lyse (CN-Free) (5 Mos./Room Temperature) | — | — | — | — | — | — | — | — | — | — | — | — | — | — | — | — |
| Experimental Lyse (CN-Free) (6 Mos./Room Temperature) | 15.3 | 10.2 | 14.3 | 4.3 | 13.7 | 5.3 | 15.4 | 5.8 | — | — | — | — | — | — | — | — |
| Experimental Lyse (CN-Free) (6 Months/60° C.) | 15.3 | 10.3 | 14 | 4.2 | 13.5 | 5.1 | 15.4 | 5.9 | — | — | — | — | — | — | — | — |
| Experimental Lyse (CN-Free) (7 Months/60° C.) | — | — | — | — | — | — | — | — | 13.9 | 4.7 | 13 | 5.8 | 14.2 | 4.6 | 14.7 | 6 |
| Experimental Lyse (CN-Free) (8 Months/60° C.) | 15.7 | 10.5 | 14.2 | 4.1 | 13.8 | 5.4 | 15.3 | 5.8 | — | — | — | — | — | — | — | — |
| Experimental Lyse (CN-Free) (9 Months/60° C.) | — | — | — | — | — | — | — | — | 13.9 | 4.9 | 13.1 | 5.8 | 14.3 | 4.6 | 14.6 | 6 |
| Experimental Lyse (CN-Free) (10 Months/60° C.) | — | — | — | — | — | — | — | — | — | — | — | — | — | — | — | — |
| Experimental Lyse (CN-Free) (11 Months/60° C.) | — | — | — | — | — | — | — | — | — | — | — | — | — | — | — | — |
| Experimental Lyse (CN-Free) (12 Months/60° C.) | — | — | — | — | — | — | — | — | — | — | — | — | — | — | — | — |
| Experimental Lyse (CN-Free) (15 Months/60° C.) | — | — | — | — | — | — | — | — | — | — | — | — | — | — | — | — |

| CD-1600 | FRESH BLOOD | | | | | | | | | | | |
|---|---|---|---|---|---|---|---|---|---|---|---|---|
| | 9 | | 10 | | 11 | | 12 | | 13 | | 14 | |
| METHOD/LYSE (TIME/TEMP.) | Hb g/dL | WBC K/μL | Hb g/dL | WBC K/μL | Hb g/dL | WBC K/μL | Hb g/dL | WBC K/μL | Hb g/dL | WBC K/μL | Hb g/dL | WBC K/μL |
| Reference Lyse (CN) 405 (Current/Room Temperature) | 16.9 | 8.9 | 13.8 | 7 | 12.8 | 8.6 | 15.7 | 5.8 | 15.6 | 3.3 | 14.6 | 6 |
| Experimental Lyse (CN-Free) (3 Mos./Room Temperature) | — | — | — | — | — | — | — | — | — | — | — | — |
| Experimental Lyse (CN-Free) (4 Mos./Room Temperature) | — | — | — | — | — | — | — | — | — | — | — | — |
| Experimental Lyse (CN-Free) (5 Mos./Room Temperature) | 16.9 | 8.8 | 13.9 | 6.8 | 12.7 | 8.3 | — | — | — | — | — | — |
| Experimental Lyse (CN-Free) (6 Mos./Room Temperature) | — | — | — | — | — | — | 15.7 | 5.6 | 15.5 | 3.3 | 14.5 | 5.9 |
| Experimental Lyse (CN-Free) (6 Months/60° C.) | — | — | — | — | — | — | — | — | — | — | — | — |
| Experimental Lyse (CN-Free) (7 Months/60° C.) | — | — | — | — | — | — | — | — | — | — | — | — |
| Experimental Lyse (CN-Free) (8 Months/60° C.) | 17.1 | 8.9 | 13.8 | 6.9 | 12.9 | 8.6 | — | — | — | — | — | — |
| Experimental Lyse (CN-Free) (9 Months/60° C.) | — | — | — | — | — | — | 15.6 | 5.7 | 15.8 | 3.5 | 14.6 | 5.8 |
| Experimental Lyse (CN-Free) (10 Months/60° C.) | 17.2 | 8.9 | 14 | 6.8 | 13.1 | 8.6 | — | — | — | — | — | — |
| Experimental Lyse (CN-Free) (11 Months/60° C.) | — | — | — | — | — | — | 15.8 | 5.7 | 15.7 | 3.3 | 14.7 | 5.8 |
| Experimental Lyse (CN-Free) (12 Months/60° C.) | 15.9 | 9.6 | 15.2 | 6.6 | 13.8 | 5.5 | — | — | — | — | — | — |
| Experimental Lyse (CN-Free) (15 Months/60° C.) | 15.9 | 9.7 | 15.2 | 6.5 | 13.9 | 5.4 | — | — | — | — | — | — |

EXAMPLE 15

Using the experimental lyse prepared according to Example 1 and the reference lyse (Cell-Dyn® Rapid Lyse), hemoglobin and WBC counts were performed using the Cell-Dyn® 1600 and Hematronics HMA Control Blood Samples (Low Control L-16321, Normal control N-16321 and High Control H-16321) (Hematronics, Santa Clara, Calif.). The purpose of this study was to evaluate the stability of the experimental lyse over time and in a temperature stressed condition. The results reported in Table 17 demonstrate that the experimental lyse, stressed at 60° C. for thirteen months and at room temperature for 20 months, still maintains comparable performance to the reference lyse.

TABLE 17

| CD-1600 | HMA CONTROLS | | | | | |
|---|---|---|---|---|---|---|
| | LOW | | NORMAL | | HIGH | |
| METHOD/LYSE (Lyse/Temperature) | Hb (g/DL) *6.8–7.4 | WBC (K/µL) *2.3–2.9 | Hb (g/DL) 13.1–13.9 | WBC (K/µL) 8.1–9.1 | Hb (g/DL) 16.5–17.5 | WBC (K/µL) 24.2–27.2 |
| Reference Lyse (CN) 405 (Current/Room Temperature) R. T./Real Time Stability | 7.1 | 2.6 | 13.3 | 8.6 | 16.8 | 25.8 |
| Experimental Lyse (CN-Free) (6 Months/Room Temperature | 7.1 | 2.7 | 13.3 | 8.5 | 16.6 | 25.5 |
| Experimental Lyse (CN-Free) (9 Months/Room Temperature | 7.1 | 2.6 | 13.3 | 8.6 | 16.7 | 25.8 |
| Experimental Lyse (CN-Free) (16 Months/Room Temperature | 7.0 | 2.8 | 13.3 | 8.8 | 16.6 | 25.8 |
| Experimental Lyse (CN-Free) (17 Months/Room Temperature | 7.0 | 2.7 | 13.2 | 8.6 | 16.6 | 25.8 |
| Experimental Lyse (CN-Free) (18 Months/Room Temperature | 6.9 | 2.7 | 13.1 | 8.8 | 16.4 | 25.8 |
| Experimental Lyse (CN-Free) (19 Months/Room Temperature | 6.9 | 2.6 | 13.1 | 8.6 | 16.4 | 25.4 |
| Experimental Lyse (CN-Free) (19 Months/Room Temperature | 6.9 | 2.7 | 13.2 | 8.6 | 16.5 | 26.1 |
| Experimental Lyse (CN-Free) (20 Months/Room Temperature 60° C. Stressed Stability | 6.7 | 2.7 | 13.1 | 8.8 | 16.4 | 26.3 |
| Experimental Lyse (CN-Free) (9 Months/60° C.) | 6.9 | 2.7 | 13.2 | 8.6 | 16.6 | 25.8 |
| Experimental Lyse (CN-Free) (10 Months/60° C.) | 6.9 | 2.7 | 13.2 | 8.7 | 16.5 | 26.0 |
| Experimental Lyse (CN-Free) (11 Months/60° C.) | 7.0 | 2.7 | 13.3 | 8.6 | 16.7 | 25.7 |
| Experimental Lyse (CN-Free) (12 Months/60° C.) | 7.0 | 2.7 | 13.2 | 8.7 | 16.5 | 26.1 |
| Experimental Lyse (CN-Free) (13 Months/60° C.) | 6.8 | 2.7 | 13.1 | 8.4 | 16.5 | 25.7 |

HMA Controls: Cell-Dyn-16, (Low Control/L-16321; Normal Control/N-16321; High Control/H-16321 F)
*Expected Mean Range Value
CN = Cyanide; CN-Free = Cyanide-Free

EXAMPLE 16

Using the experimental lyse prepared according to Example 1 and the reference lyse (Cell-Dyn® Rapid Lyse), hemoglobin and WBC counts were performed using the Cell-Dyn® 1600 and HMA Control Blood Samples (Low Control L-16311, Normal control N-16311 and High Control H-16311). The purpose of this study was to evaluate the stability of the experimental lyse over time after refrigerated storage (2° to 5° C.) for eight months. The lyse was warmed to room temperature before use. The results reported in Table 18 demonstrate that the experimental lyse, stored at 2–5° C. for up to eight months still maintains performance comparable to the reference lyse.

TABLE 18

| | FRESH BLOOD | | | | | | HMA CONTROL | | | | | |
|---|---|---|---|---|---|---|---|---|---|---|---|---|
| | 1 | | 2 | | 3 | | Low | | Normal | | High | |
| | HB | WBC | HB | WBC | HB | WBC | HB g/dL 7.1 ± 0.3 | WBC K/µL 2.6 ± 0.3 | HB g/dL 12.8 ± 0.4 | WBC K/µL 9.0 ± 0.5 | HB g/dL 17.2 ± 0.5 | WBC K/µL 23.2 ± 0.5 |
| | g/dL | K/µL | g/dL | K/µL | g/dL | K/µL | | | | | | |
| Reference Lyse (405) | 16.9 | 8.9 | 13.8 | 7 | 12.8 | 8.6 | 7 | 2.6 | 12.7 | 9 | 16.9 | 23.2 |
| Experimental Lyse | 16.9 | 8.8 | 13.9 | 6.8 | 12.7 | 8.3 | 7.1 | 2.4 | 12.7 | 9 | 16.8 | 23.1 |
| Experimental Lyse (8 months/2–5° C.) | 16.8 | 8.9 | 13.9 | 7.1 | 12.9 | 8.6 | 7.1 | 2.7 | 12.8 | 9.2 | 16.9 | 23.2 |

EXAMPLE 17

Using the experimental lyse prepared according to Example 1 and the reference lyse (Cell-Dyn® Rapid Lyse), hemoglobin and WBC counts were performed using the Cell-Dyn® 1600 and HMA Control Blood Samples (Low Control L-16311, Normal control N-16311 and High Control H-16311). The purpose of this study was to evaluate the stability of the experimental lyse over time after freezing twice and thawing. The results reported in Table 19 demonstrate that the experimental lyse, stored at −5° to −8° C. and then warmed to room temperature twice during eight months still maintains performance comparable to the reference lyse.

EXAMPLE 19

Diluent No. 1 was used to dilute the whole blood samples. Lysing agents for use in the Cell-Dyn® 900 instrument were made by adding to 10 mL of deionized water. The formulations are listed in Table 21. Stability results of lyse reagent formulation #4 as compared to the reference lyse are shown in Table 22. The results of the experimental multipurpose lyse of the present invention was comparable to the reference lyse.

TABLE 19

| | FRESH BLOOD | | | | | | HMA CONTROL | | | | | |
| | | | | | | | Low | | Normal | | High | |
| | 1 | | 2 | | 3 | | HB | WBC | HB | WBC | HB | WBC |
| | HB g/dL | WBC K/µL | HB g/dL | WBC K/µL | HB g/dL | WBC K/µL | g/dL 7.1 ± 0.3 | K/µL 2.6 ± 0.3 | g/dL 12.8 ± 0.4 | K/µL 9.0 ± 0.5 | g/dL 17.2 ± 0.5 | K/µL 23.2 ± 0.5 |
|---|---|---|---|---|---|---|---|---|---|---|---|---|
| Reference Lyse (405) | 16.9 | 8.9 | 13.8 | 7 | 12.8 | 8.6 | 7 | 2.6 | 12.7 | 9 | 16.9 | 23.2 |
| Experimental Lyse (5 Months/RT) | 16.9 | 8.8 | 13.9 | 6.8 | 12.7 | 8.3 | 7.1 | 2.4 | 12.7 | 9 | 16.8 | 23.1 |
| Experimental Lyse (Frozen thawed twice) | 16.7 | 8.7 | 13.8 | 6.7 | 12.8 | 8.4 | 7.1 | 2.6 | 12.8 | 9.1 | 17 | 23.3 |

EXAMPLE 18

Using the Multi-purpose lyse reagent prepared according to Example 1 and the reference lyse (Cell-Dyn® Rapid Lyse), hemoglobin and WBC counts were performed using the Cell-Dyn® 1600 S/P Diff-Trol (Baxter) hematology Control Blood Samples (Abnormal Low SV31L, Norman Control SV31N and Abnormal High Control SV31H); Para 12 Plus (Streck) Hematology Control Blood Samples (Abnormal Low 2512PL, Normal 2512PN and High Abnormal 2512PH); and fresh blood as a reference. The purpose of this study was to compare the performance of the experimental lyse with hematology controls from other manufacturers. The results reported in Table 20 demonstrate that the experimental lyse exhibits performance comparable with the reference lyse for the controls tested.

TABLE 21

| Lysing Reagent # | Hydroxylamine HCl | TTAB |
|---|---|---|
| 1 | 0.4 g | 2.0 g |
| 2 | 0.8 g | 2.0 g |
| 3* | 2.0 g | 10.0 g |
| 4* | 4.0 g | 10.0 g |
| 5 | 1.5 g | 2.0 g |

*50 mL of deionized water used.

TABLE 20

| | S/P DIFF-TROL (Baxter) | | | | | | PARA 12 PLUS (StrecK) | | | | | | FRESH BLOOD | | | | | |
| | 1 | | 2 | | 3 | | 1 | | 2 | | 3 | | 1 | | 2 | | 3 | |
| CD-1600 METHOD/LYSE | Hb g/dL | WBC K/µL | Hb g/dL | WBC K/µL | Hb g/dL | WBC K/µL | Hb g/dL | WBC K/µL | Hb g/dL | WBC K/µL | Hb g/dL | WBC K/µL | Hb g/dL | WBC K/µL | Hb g/dL | WBC K/µL | Hb g/dL | WBC K/µL |
|---|---|---|---|---|---|---|---|---|---|---|---|---|---|---|---|---|---|---|
| Reference Lyse (CN/405) | 6.1 | 2.1 | 13.3 | 10.1 | 17.8 | 20.5 | 7.3 | 8.3 | 14.4 | 22.4 | 19.8 | 22.4 | 12.7 | 3.9 | 13.6 | 4.8 | 15.8 | 5.5 |
| Experimental Lyse (CN-Free) | 6.1 | 2.1 | 13.2 | 10.2 | 17.6 | 20.8 | 7.2 | 8.3 | 14.1 | 22.6 | 19.5 | 22.6 | 12.6 | 4.1 | 13.5 | 5 | 15.7 | 5.7 |

TABLE 22

Stability Study of Cyanide-Free Rapid Lyse on Cell-Dyn 900 with Whole Blood Samples

| CD-900 METHOD/LYSE | Blood #1 | | | | Blood #2 | | | |
|---|---|---|---|---|---|---|---|---|
| | Hb (g/dL) | | WBC (K/uL) | | Hb (g/dL) | | WBC (K/uL) | |
| (Time/Temperature) | *1 min | *5 min | 1 min | 5 min | 1 min | 5 min | 1 min | 5 min |
| Reference Lyse (CN) (Current/Room Temperature) | 14.4 | 14.4 | 5.1 | 5.0 | 15.4 | 15.4 | 5.2 | 5.1 |
| Experimental Lyse (CN-Free) (15 days/Room Temperature) | 14.3 | 14.2 | 5.3 | 5.1 | 15.5 | 15.3 | 5.3 | 5.1 |
| Experimental Lyse (CN-Free) (4 months/Room Temperature) | 14.4 | 14.3 | 5.3 | 5.0 | 15.5 | 15.4 | 5.2 | 5.1 |
| Experimental Lyse (CN-Free) (2 years/Room Temperature) | 14.3 | 14.2 | 5.2 | 5.1 | 15.5 | 15.3 | 5.3 | 4.9 |
| Experimental Lyse (CN-Free) (3 months/60 C.) | 14.3 | 14.1 | 5.2 | 5.0 | 15.4 | 15.3 | 5.3 | 5.0 |

EXAMPLE 20

Figure 5:
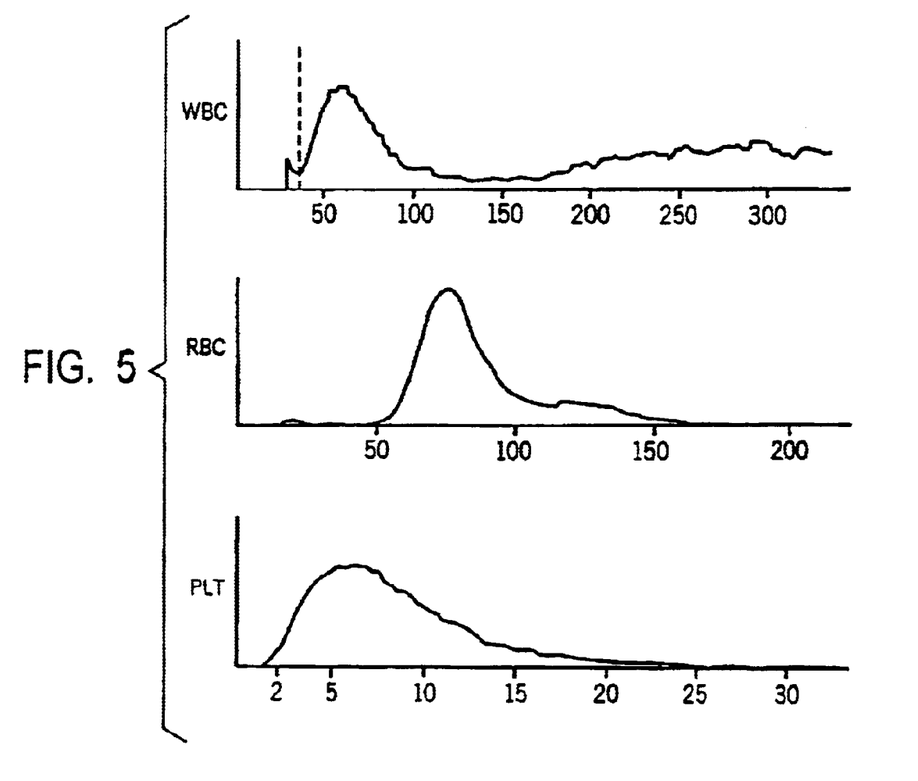
FIG. 5 is a plot graph of a triphasic distribution of the subpopulations of white blood cells in a normal whole blood sample.

Lysing reagents formulations for use in the Cell-Dyn® 610, 1400, 1500, 1600, and 2000 instruments were made by adding to 1000 mL of deionized water the components listed in Table 23. Stability results of the lyse reagent formulation #7 as compared to the reference lyse are shown in Table 24. In addition, the formulation of lyse reagent #7 in Table 23 produced the cyanide free differential plot graph of FIG. 5.

TABLE 23

| Lysing Reagent Formulation # | Hydroxylamine HCl | Dodecyltrimethyl ammonium chloride (50%) | TTAB |
|---|---|---|---|
| 1 | 1.5 g | 71.3 g | — |
| 2 | 1.5 g | 87.3 g | — |
| 3 | 0.75 g | 71.3 g | — |
| 4 | 0.75 g | 87.3 g | — |
| 5 | 1.5 g | 60.0 g | 2.0 g |
| 6 | 2.0 g | 50.0 g | 2.5 g |
| 7 | 1.5 g | 60.0 g | 1.5 g |
| 8 | 2.0 g | 50.0 g | 2.0 g |

TABLE 24

Stability Study of Cyanide-Free Diff. Lyse on Cell-Dyn 1600 with Whole Blood Samples

| CD-1600 METHOD/LYSE | Blood #1 | | Blood #2 | | Blood #3 | |
|---|---|---|---|---|---|---|
| | Hb g/dL | WBC K/uL | Hb g/dL | WBC K/uL | Hb g/dL | WBC K/uL |
| Reference Lyse (Cyanide) 420 (Current) | 15.5 | 7.6 | 15.3 | 8.9 | 14.8 | 10.8 |
| Experimental Lyse (CN-Free) (25 days) | 15.5 | 7.7 | 15.5 | 8.8 | 14.8 | 10.7 |
| Experimental Lyse (CN-Free) (3 months) | 15.5 | 7.7 | 15.4 | 8.8 | 14.9 | 10.8 |
| Experimental Lyse (CN-Free) (4 months) | 15.5 | 7.7 | 15.4 | 8.8 | 14.7 | 10.7 |

EXAMPLE 21

Lysing reagent for use in the Cell-Dyn® 3000 instrument was made by adding to 1000 mL of deionized water 10 g of benzalkonium chloride (50%), 10 g of dodecyltrimethyl ammonium chloride (50%), 2.35 g hydroxylamine hydrochloride and 4.5 g NaCl.* Stability results of the lyse reagent formulation compared to the reference lyse is shown in Table 25.

*The NaCl was added to increase the conductivity of the liquid reagents utilized in the instrument.

As shown, the results of the experimental multipurpose lyse of the present invention has comparable performance as the reference lyse. Alternatively, 20 g of benzalkonium chloride (50%), 20 g of dodecyltrimethyl ammonium chloride (50%), 4.7 g hydroxylamine hydrochloride and 9.0 g NaCl can be used.

TABLE 25

Stability of Cyanide-Free Lyse on Cell-Dyn 3000 with Whole Blood Samples

| CD-3000 METHOD/LYSE (Time/Temperature) | Fresh Blood | | | | | | | | | |
|---|---|---|---|---|---|---|---|---|---|---|
| | #1 | #2 | #3 | #4 | #5 | #6 | #7 | #8 | #9 | #10 |
| | Hb (g/dL) | | | | | | | | | |
| Reference Lyse (CN) 411 (Current/Room Temperature) | 14.5 | 15.7 | 15.3 | 15.9 | 14.6 | 14.1 | 14.0 | 15.1 | 14.0 | 13.6 |
| Experimental Lyse (CN-Free) (2 months/Room Temp.) | 14.5 | 15.6 | 15.0 | 15.8 | — | — | — | — | — | — |

TABLE 25-continued

Stability of Cyanide-Free Lyse on Cell-Dyn 3000 with Whole Blood Samples

| | | | | | | | | | |
|---|---|---|---|---|---|---|---|---|---|
| Experimental Lyse (CN-Free) (6 months/Room Temp.) | — | — | — | — | 14.6 | 14.0 | 14.0 | — | — | — |
| Experimental Lyse (CN-Free) (9 months/Room Temp.) | — | — | — | — | 14.5 | 14.2 | 13.9 | — | — | — |
| Experimental Lyse (CN-Free) (11 months/Room Temp.) | — | — | — | — | — | — | — | 15.1 | 14.1 | 13.7 |
| Experimental Lyse (CN-Free) (13 months/Room Temp.) | 14.7 | 15.8 | 15.1 | 15.9 | — | — | — | — | — | — |
| Experimental Lyse (CN-Free) (16 months/Room Temp.) | — | — | — | — | — | — | — | — | — | — |
| Experimental Lyse (CN-Free) (19 months/Room Temp.) | — | — | — | — | — | — | — | — | — | — |
| Experimental Lyse (CN-Free) (5 months/60 C.) | 14.5 | 15.7 | 15.0 | 15.9 | — | — | — | — | — | — |
| Experimental Lyse (CN-Free) (7 months/60 C.) | 14.6 | 15.6 | 15.0 | 15.9 | — | — | — | — | — | — |
| Experimental Lyse (CN-Free) (9 months/60 C.) | — | — | — | — | — | — | — | 15.0 | 14.1 | 13.8 |
| Experimental Lyse (CN-Free) (11 months/60 C.) | — | — | — | — | — | — | — | — | — | — |
| Experimental Lyse (CN-Free) (12 months/60 C.) | — | — | — | — | — | — | — | — | — | — |
| Experimental Lyse (CN-Free) (15 months/60 C.) | — | — | — | — | — | — | — | — | — | — |
| Experimental Lyse (CN-Free) (18 months/60 C.) | — | — | — | — | — | — | — | — | — | — |

| | Fresh Blood | | | | | | | | |
|---|---|---|---|---|---|---|---|---|---|
| CD-3000 Method/LYSE (Time/Temperature) | #11 | #12 | #13 | #14 | #15 Hb (g/dL) | #16 | #17 | #18 | #19 |
| Reference Lyse (CN) 411 (Current/Room Temperature) | 12.8 | 16.2 | 14.3 | 13.6 | 14.5 | 14.2 | 12.9 | 15.3 | 15.2 |
| Experimental Lyse (CN-Free) (2 months/Room Temp.) | — | — | — | — | — | — | — | — | — |
| Experimental Lyse (CN-Free) (6 months/Room Temp.) | — | — | — | — | — | — | — | — | — |
| Experimental Lyse (CN-Free) (9 months/Room Temp.) | 12.6 | 16.0 | 14.2 | — | — | — | — | — | — |
| Experimental Lyse (CN-Free) (11 months/Room Temp.) | — | — | — | — | — | — | — | — | — |
| Experimental Lyse (CN-Free) (13 months/Room Temp.) | — | — | — | — | — | — | — | — | — |
| Experimental Lyse (CN-Free) (16 months/Room Temp.) | — | — | — | 13.6 | 14.5 | 14.0 | — | — | — |
| Experimental Lyse (CN-Free) (19 months/Room Temp.) | — | — | — | — | — | — | 13.1 | 15.2 | 15.2 |
| Experimental Lyse (CN-Free) (5 months/60 C.) | — | — | — | — | — | — | — | — | — |
| Experimental Lyse (CN-Free) (7 months/60 C.) | — | — | — | — | — | — | — | — | — |
| Experimental Lyse (CN-Free) (9 months/60 C.) | — | — | — | — | — | — | — | — | — |
| Experimental Lyse (CN-Free) (11 months/60 C.) | 12.6 | 15.9 | 14.2 | — | — | — | — | — | — |
| Experimental Lyse (CN-Free) (12 months/60 C.) | 12.6 | 15.9 | 14.2 | — | — | — | — | — | — |
| Experimental Lyse (CN-Free) (15 months/60 C.) | — | — | — | 13.5 | 14.6 | 14.2 | — | — | — |
| Experimental Lyse (CN-Free) (18 months/60 C.) | — | — | — | — | — | — | 13.2 | 15.5 | 15.5 |

EXAMPLE 22

Four fresh whole blood samples were first analyzed on the Coulter S-Plus IV® Hematology Analyzer with standard Coulter reagents. The multipurpose lyse reagent was then used in the place of the Coulter lyse and the same whole blood samples run on the Coulter Analyzer. The results of the multipurpose cyanide-free lyse of the present invention were comparable with the standard Coulter reagents. The formulation used was Formulation #7 in Table 23. Results are shown in Table 26.

TABLE 26

Comparison Study of Cyanide-Free Diff Lyse with Coulter reference Reagent on Coulter S-Plus IV Hematology Analyzer

| Coulter S-Plus IV METHOD/LYSE | Blood #1 | | Blood #2 | | Blood #3 | | Blood #4 | |
|---|---|---|---|---|---|---|---|---|
| | Hb g/dL | WBC K/uL | Hb g/dL | WBC K/uL | Hb g/dL | WBC K/uL | Hb g/dL | WBC K/uL |
| Coulter Reference Lyse (Lot 101698 F) | 14.0 | 8.5 | 14.3 | 7.1 | 13.7 | 5.1 | 15.9 | 5.7 |
| Cyanide Free Diff Lyse (SK 976002) | 13.9 | 8.6 | 14.2 | 7.2 | 13.6 | 5.1 | 15.7 | 5.7 |

We claim:

1. A multi-purpose, cyanide-free lyse reagent for making hemoglobin (Hb) and leukocyte (WBC) determinations comprising, in combination:
   (a) an aqueous multipurpose lyse reagent comprising at least one quaternary ammonium salt, said quaternary salt selected from the group consisting of: tetradecyltrimethyl ammonium bromide (TTAB), dodecyltrimethyl ammonium chloride, cetyl trimethyl ammonium bromide, hexadecyltrimethyl ammonium bromide, benzalkonium chloride, and cetylpyridium chloride; and
   (b) at least one hydroxylamine salt selected from the group consisting of: hydrochloride, sulfate, phosphate, and other acid salts; wherein said multipurpose lyse reagent produces a chromogen having maximum absorbance between 530 and 550 nm.

2. An aqueous, cyanide-free multipurpose lyse reagent for making hemoglobin (Hb) and leukocyte (WBC) determinations comprising, in combination:
   (a) 10–20% (wt) of at least one quaternary ammonium salt selected from the group consisting of: tetradecyltrimethyl ammonium bromide (TTAB), dodecyltrimethyl ammonium chloride, cetyltrimethyl ammonium bromide, benzalkonium chloride, and cetylpyridium chloride; and
   (b) 2–15% (wt) of at least one hydroxylamine salt, said at least one hydroxylamine salt selected from the group consisting of: hydrochloride, sulfate, phosphate and other acid salts;
   wherein said multipurpose lyse reagent produces a chromogen having maximum absorbance between 530 and 550 nm.

3. An aqueous, cyanide-free multipurpose lyse reagent for making hemoglobin (Hb) and leukocyte (WBC) determinations comprising, in combination:
   (a) 2–10% (wt) of benzalkonium chloride and 2–10% (wt) of dodecyltrimethyl ammonium chloride; and
   (b) 1–5% (wt) of at least one hydroxylamine salt, said at least one hydroxylamine salt selected from the group consisting of: hydrochloride, sulfate, phosphate and other acid salts;
   wherein said multipurpose lyse reagent produces a chromogen having maximum absorbance between 530 and 550 nm.

4. An aqueous, cyanide-free multipurpose lyse reagent for making hemoglobin (Hb) and leukocyte (WBC) determinations comprising, in combination:
   (a) 0–1% (wt) of tetradecyltrimethyl ammonium bromide (TTAB) and 2-10% (wt) of dodecyltrimethyl ammonium chloride; and
   (b) 0.1–1% (wt) of at least one hydroxylamine salt, said at least one hydroxylamine salt selected from the group consisting of: hydrochloride, sulfate, phosphate and other acid salts;
   wherein said multipurpose lyse reagent produces a chromogen having maximum absorbance between 530 and 550 nm.

5. An aqueous, cyanide-free multipurpose lyse reagent for making hemoglobin (Hb) and leukocyte (WBC) determinations comprising, in combination:
   (a) 0.1–5% (wt) of benzalkonium chloride and 0.1–5% (wt) of dodecyltrimethyl ammonium chloride; and
   (b) 0.1–1% (wt) of at least one hydroxylamine salt, said at least one hydroxylamine salt selected from the group consisting of: hydrochloride, sulfate, phosphate and other acid salts;
   wherein said multipurpose lyse reagent produces a chromogen having maximum absorbance between 530 and 550 nm.

* * * * *